(12) United States Patent
Güthner et al.

(10) Patent No.: US 6,620,932 B2
(45) Date of Patent: Sep. 16, 2003

(54) 2-ALKOXY-5-METHOXYPYRIMIDINES OR THEIR TAUTOMERIC FORMS AND METHODS FOR PRODUCING THE SAME

(75) Inventors: Thomas Güthner, Trostberg (DE); Karl-Heinz Neuhauser, Trostberg (DE)

(73) Assignee: Degussa AG, Trostberg (DE)

( * ) Notice: Subject to any disclaimer, the term of this patent is extended or adjusted under 35 U.S.C. 154(b) by 0 days.

(21) Appl. No.: 10/203,917

(22) PCT Filed: Apr. 17, 2001

(86) PCT No.: PCT/EP01/04345

§ 371 (c)(1),
(2), (4) Date: Aug. 15, 2002

(87) PCT Pub. No.: WO01/81320

PCT Pub. Date: Nov. 1, 2000

(65) Prior Publication Data

US 2003/0022908 A1 Jan. 30, 2003

(30) Foreign Application Priority Data

Apr. 19, 2000 (DE) .......................................... 100 19 291

(51) Int. Cl.$^7$ ............................................. C07D 239/52
(52) U.S. Cl. ....................................... 544/314; 544/318
(58) Field of Search ................................. 544/318, 314

(56) References Cited

U.S. PATENT DOCUMENTS 4,125,720 A    11/1978    Pesson et al. ................ 544/318
6,362,335 B2 *  3/2002   Emonds et al. ............. 544/263

FOREIGN PATENT DOCUMENTS

DE    34 41 369 A1    5/1986
DE    40 29 648 A     3/1992

OTHER PUBLICATIONS

Pyrimidines Part XI, Synthesis of 5–Hydroxypyrimidine and Related Compounds, Chesterfield, et al. J. Chem. Soc. 1960, pp. 4590–4596.
Pyrimidines X. Synthesis of bacimethrin, 2–Methoxy . . . Alkoxypyrimidines, Koppel, et al., J. Org. Chem. 1962, pp. 3614–3617.
Chem. Abstract 96, Nr. 180550 (1982).

* cited by examiner

*Primary Examiner*—John M. Ford
(74) *Attorney, Agent, or Firm*—Fulbright & Jaworski L.L.P.

(57) ABSTRACT

Novel 2-alkoxy-5-methoxypyrimidines and tautomeric forms thereof and also processes for preparing them are described. The 2-alkoxy-5-methoxypyrimidines according to the invention can be synthesized in few reaction steps and in high yields from simple precursors.

24 Claims, No Drawings

2-ALKOXY-5-METHOXYPYRIMIDINES OR THEIR TAUTOMERIC FORMS AND METHODS FOR PRODUCING THE SAME

The present invention relates to 2-alkoxy-5-methoxypyrimidines, tautomeric forms thereof and processes for preparing them.

5-Methoxypyrimidines are important intermediates in preparing active pharmaceutical and agrochemical ingredients. In many cases, the active ingredient, as well as other substituents, additionally contains a 2-alkoxy group. Such applications are mentioned, for example, in the documents U.S. Pat. No. 5,163,955, DE-OS 40 29 648, FR-A 1 33 318 and in Collect. Czech. Chem. Commun. 59(2), 482 (1994).

These 5-methoxypyrimidines which, as well as other substituents, contain a 2-alkoxy group can be prepared by various routes. For example, Z. Budezinski et al., Cesk. Farm. 10, 241 (1961) describe the synthesis of this type of active ingredient which comprises first preparing a 2-methylmercapto-4-hydroxy-5-methoxy-pyrimidine, then converting it to the corresponding 2,4-dihydroxypyrimidine derivative, subsequently carrying out a chlorination to give the 2,4-dichloropyrimidine derivative and finally reacting it in a plurality of steps to give the 2-methoxy-4-amino-5-methoxypyrimidine.

A disadvantage of this preparation process is the extremely long reaction sequence which additionally, owing to the lack of regioselectivity between the 2 and 4 positions on the pyrimidine ring, is prone to isomer formation and, besides, only delivers low overall yields.

It is accordingly an object of the present invention to provide novel 2-alkoxy-5-methoxypyrimidines and tautomeric forms thereof which are industrially relatively simple to prepare in high yields. According to the invention, this object is achieved by the 2-alkoxy-5-methoxypyrimidines according to claim 1.

It has been found that, surprisingly, the 2-alkoxy group may be introduced into the appropriate pyrimidine derivatives even at the start of the reaction sequence and that the 4 substituent can be converted and exchanged in a simple manner without isomeric by-products resulting.

The 2-alkoxy-5-methoxypyrimidines according to the invention conform to the general formula (I)

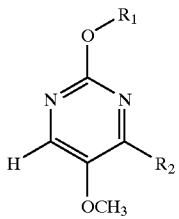

(I)

and include their tautomeric forms. In the formula (I)
  $R_1$ is a linear or branched and optionally unsaturated aliphatic hydrocarbon radical having from 1 to 5 carbon atoms and
  $R_2$=OH, F, Cl, Br or —$SO_xR_3$ where $R_3$=$C_1$–$C_4$-alkyl and x=0, 1 or 2.

Particular preference is given to 2-alkoxy-5-methoxypyrimidines where $R_1$=$CH_3$ and $R_2$=OH or $R_1$=$CH_3$ and $R_2$=Cl.

The 2-alkoxy-5-methoxypyrimidines according to the invention can be synthesized in few reaction steps and in high yields from simple precursors. For example, 2-alkoxy-4-hydroxy-5-methoxypyrimidines can be prepared by reacting an alkyl ester of 3-hydroxy-2-methoxyacrylic acid or of its tautomeric forms or an alkali metal salt of the ester with an O-alkylisourea or a corresponding salt.

Preferred alkyl esters of 3-hydroxy-2-methoxyacrylic acid (or of its tautomeric forms or alkali metal salts) are the corresponding methyl and ethyl esters. Preference is given to preparing these compounds from methoxyacetic esters in a known manner and reacting them without isolation and further purification.

Preferred alkali metal salts of the alkyl 3-hydroxy-2-methoxyacrylate ester are the sodium or potassium salt thereof. The O-alkylisourea compounds used are in particular those of O-methylisourea and O-ethylisourea or salts thereof. In particular, O-methylisourea sulfate, O-methylisourea hydrogensulfate, the free O-methylisourea base, O-ethylisourea hydrochloride, O-ethylisourea hydrogensulfate and the free O-ethylisourea base are used.

The 3-hydroxy-2-methoxyacrylic ester is reacted with the O-alkylisourea derivative in aqueous and/or alcoholic solution in the presence of a base.

The alcohols used are preferably $C_1$–$C_4$-alcohols, in particular methanol or ethanol. The bases used are preferably the free O-alkylisourea, sodium hydroxide, sodium methoxide or sodium ethoxide.

The molar ratio of the alkyl 3-hydroxy-2-methoxyacrylate ester to the O-alkylisourea derivative may vary within a wide range, but it has proven particularly advantageous to set this ratio to from 1:2 to 2:1. Also, preference is given to using from 1 to 5 mol of base per mole of the desired pyrimidine compound.

It is to be regarded as essential to the invention that the reaction of the alkyl 3-hydroxymethoxyacrylate ester (or its tautomeric forms or alkali metal salts) with the O-alkylisourea (salt) be carried out at temperatures of from 20 to 100° C., in particular from 40 to 80° C. The reaction time may vary within a wide range, but for economic reasons it is preferably from 2 to 12 h.

The 2-alkoxy-4-hydroxy-5-methoxypyrimidines obtained in this way are preferably precipitated out of the reaction mixture by adjusting the pH to from 2.0 to 8.0 and removed by customary methods, for example by filtration.

These 2-alkoxy-4-hydroxy-5-methoxypyrimidines can be reacted directly with, for example, phosphorus oxy-chloride to give 2-alkoxy-4-chloro-5-methoxypyrimidines or with phosphorus oxybromide to give the corresponding 2-alkoxy-4-bromo-5-methoxypyrimidines.

This reaction is effected in particular with the addition of an excess of the appropriate phosphorus oxychloride or phosphorus oxybromide, and auxiliary bases or solvents may be used if necessary.

Preference is given to using from 2 to 8 mol of phosphorus oxychloride or phosphorus oxybromide per mole of 2-alkoxy-4-hydroxy-5-methoxypyrimidines. Examples of useful auxiliary bases include triethylamine, dimethylaniline and diethylaniline. These auxiliary bases are used in a quantity of from 0 to 1 mol of auxiliary base per mole of 2-alkoxy-4-hydroxy-5-methoxypyrimidines.

In principle, useful solvents include all organic solvents which are inert toward phosphorus oxychloride or phosphorus oxybromide, for example, toluene, xylene, hexane, cyclohexane or dichloromethane. The corresponding reaction is effected at a temperature of from 40 to 120° C., preferably from 70 to 110° C.

The 2-alkoxy-4-chloro-5-methoxypyrimidines according to the invention and the similarly preparable 2-alkoxy-4-bromo-5-methoxypyrimidines can be converted by customary subsequent reactions, for example, conversion to the corresponding 2-alkoxy-4-fluoro-5-methoxypyrimidines by reacting with potassium fluoride or sodium fluoride. Similarly, reaction with the thiols R₃SR or its alkali metal salts thereof may be effected in an organic solvent at temperatures of from 40 to 120° C. If desired, the mercapto group SR₃ may then be oxidized using suitable oxidizing agents, for example, HOCl or peroxo compounds (in particular hydrogen peroxide) to give the desired —SOR₃ and —SO₂R₃ radicals. Hydrocarbons, alcohols, ethers, esters, amides and nitriles are particularly useful organic solvents for this purpose.

With the aid of this processes, the 2-alkoxy-5-methoxypyrimidines accordy to the invention can be obtained in few reaction steps, in excellent yields and in a technically simple manner.

The invention is illustrated by the following examples:

EXAMPLES

Example 1

315.5 g of methyl 2-methoxyacetate were admixed with 1485.8 g of methyl formate. 183.8 g of solid sodium methoxide were metered into this mixture at 15° C. over 90 minutes. The mixture was stirred for 22 hours at 15° C. 450 g of methanol were then added and the excess methyl formate distilled off. A methanolic suspension of the crude sodium salt of methyl 3-hydroxy-2-methoxy-acrylate was obtained.

Example 2

535.6 g of O-methylisourea sulfate (96% pure) were initially charged into 810 g of methanol. 342 g of 50% sodium hydroxide were then metered in at −5°C., the precipitated sodium sulfate filtered off and washed with methanol. The combined filtrates comprised 4.2 mol of O-methylisourea base.

Example 3

A suspension of the sodium salt of methyl 3-hydroxy-2-methoxyacrylate obtained in Example 1 was initially charged at 40° C. and the solution of O-methylisourea base obtained in Example 2 metered in over 2 hours. The mixture was then heated at 65° C. for 8 hours. 450 g of water were then added and the methanol distilled off as completely as possible. The suspension obtained was adjusted from pH 13 to pH 5 using 321 g of 37% hydrochloric acid and stirred at room temperature for 2 hours. The precipitated product was filtered off with suction, washed and dried at 60° C. under reduced pressure.

277 g of 2,5-dimethoxy-4-hydroxypyrimidine in the form of a white powder having a purity of >98% were obtained. ¹H-NMR: 3.638 ppm (s, 3H), 3.767 ppm (s, 3H), 7.272 ppm (s, 1H); ¹³C-NMR 54.22 ppm (OCH₃), 56.34 ppm (OCH₃), 129.67 ppm (C₅), 141.96 ppm (C₆), 152.90 ppm (C₄), 160.00 ppm (C₂). Elemental analysis: found C 46.05, H 5.25, N 17.85%. Mass spectrum: M⁺=156 g/mol. The yield was 59%.

Example 4

15.6 g (0.1 mol) of 2,5-dimethoxy-4-hydroxypyrimidine from Example 3 were suspended in 25 g of toluene. 46.0 g of phosphorus oxychloride were added and the suspension heated to 80° C. Within 1 hour, 20.2 g of triethylamine were added dropwise and the entire mixture was stirred at 80° C. for 30 minutes.

The entire mixture was poured into 600 g of ice-water, stirred for 12 hours and adjusted to pH 5 using sodium hydroxide. The toluene phase was removed, and the aqueous phase extracted a further 3 times with 50 mol of toluene each time. The combined toluene extracts were concentrated to dryness.

12.57 g of 4-chloro-2,5-dimethoxypyrimidine were obtained in the form of slightly yellowish crystals of characteristic odor. Melting point: 78 to 80° C., ¹H-NMR: 3.860 ppm (s, 3H), 3.909 ppm (s, 3H), 8.446 ppm (s, 1H), ¹³C-NMR: 55.11 ppm (OCH₃), 57.42 ppm (OCH₃), 143.90 ppm (C₆), 145.09 ppm (C₅), 149.67 ppm (C₄), 158.28 ppm (C₂). GC/MS data: content>98%, M⁺ 174/176 g/mol. The yield was 72%.

What is claimed is:

1. A 2-Alkoxy-5-methoxypyrimidine of the formula (I)

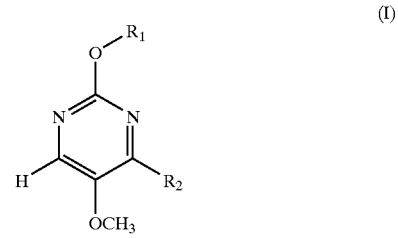

and tautomeric forms thereof where
R₁ is a linear or branched and optionally unsaturated aliphatic hydrocarbon radical having from 1 to 5 carbon atoms and
R₂=OH, F, Cl, Br or —SO$_x$R₃ where R₃=C₁–C₄-alkyl and x=0, 1 or 2.

2. A 2-Alkoxy-5-methoxypyrimidine as claimed in claim 1, wherein R₁=CH₃ and R₂=OH.

3. A 2-Alkoxy-5-methoxypyrimidine as claimed in claim 1, wherein that R₁=CH₃ and R₂=Cl.

4. A process for preparing a 2-alkoxy-5-methoxypyrimidine as claimed in claim 1, wherein R₂=OH, comprising reacting an alkyl ester of 3-hydroxy-2-methoxyacrylic acid or a tautomer thereof or an alkali metal of said alkyl ester with an O-alkylisourea or a salt thereof in at least one of an aqueous or alcoholic solution in the presence of a base at a temperature of from 20 to 100° C.

5. The process as claimed in claim 4, wherein said alkyl 3-hydroxy-2-methoxyacrylate is at least one of the methyl or ethyl ester.

6. The process as claimed in claim 4, wherein the alkali metal salt of the alkyl 3-hydroxy-3-methoxyacrylate is the sodium salt.

7. The process as claimed in claim 4, wherein said O-alkylisourea compounds or salt thereof is selected from the group consisting of O-methylisourea, O-ethylisourea and salts thereof.

8. The process as claimed in claim 4, wherein said O-alkylisourea is selected from the group consisting of O-methylisourea sulfate, O-methylisourea hydrogensulfate, the free O-methylisourea base, O-ethylisourea hydrochloride, O-ethylisourea hydrogensulfate and the free O-ethylisourea base.

9. The process as claimed in claim 4, wherein that the reaction is carried out in an alcoholic solution comprising C₁–C₄-alcohol.

10. The process as claimed in claim 4, wherein said base is selected from the group consisting of free O-alkylisourea, sodium hydroxide, sodium methoxide or sodium ethoxide.

11. The process as claimed in claim 4, wherein the molar ratio of alkyl 3-hydroxy-2-methoxyacrylate to O-alkylisourea ranges from 1:2 to 2:1.

12. The process as claimed in claim 4, wherein from 1 to 5 mol of base are present per mole of the desired pyrimidine compound.

13. The process as claimed in claim 4, wherein the reaction is carried out at a temperature of from 40 to 80° C.

14. The process as claimed in claim 4, wherein the 2-alkoxy-4-hydroxy-5-methoxypyrimidine is precipitated after complete reaction by adjusting the pH to from 2.0 to 8.0 and removed by customary methods.

15. A process for preparing a 2-alkoxy-5-methoxy-pyrimidine as claimed in claim 24, wherein $R_2$=Cl or Br, comprising reacting 2-alkoxy-4-hydroxy-5-methoxypyrimidine with excess phosphorus oxychloride or phosphorus oxybromide, optionally in the presence of at least one of an auxiliary base and a solvent at a temperatures of from 40 to 120° C.

16. The process as claimed in claim 15, wherein from 2 to 8 mol of phosphorus oxychloride or phosphorus oxybromide are present per mole of 2-alkoxy-4-hydroxy-5-methoxypyrimidine.

17. The process as claimed in claim 15, wherein said auxiliary bases are selected from the group consisting of triethylamine, dimethylaniline or diethylaniline.

18. The process as claimed in claim 15, wherein from 0.1 to 1 mol of auxiliary base is present per mole of 2-alkoxy-4-hydroxy-5-methoxypyrimidines.

19. The process as claimed in claim 15, wherein said solvent is selected from the group consisting of toluene, xylene, hexane, cyclohexane and dichloromethane.

20. The process as claimed in claim 15, wherein the reaction is carried out at a temperature of from 70 to 100° C.

21. A process for preparing a 2-alkoxy-5-methoxy-pyrimidine as claimed in claim 1, wherein $R_2$=—F or —$SO_xR_3$, comprising reacting a 2-alkoxy-4-chloro-5-methoxypyrimidine with at least one of potassium and fluoride or sodium fluoride or with a thiol of the formula $R_3SH$ or its alkali metal salts in an organic solvent at a temperature of from 40 to 120° C. and, optionally, oxidizing the mercapto group —$SR_3$ with a suitable oxidizing agent to prepare the desired —$SOR_3$ group and —$SO_2R_3$ group respectively.

22. The process as claimed in claim 21, wherein the reaction is said organic solvent is selected from the group consisting of an hydrocarbon, an alcohol, an ether, an ester, an amide and a nitrile.

23. The process as claimed in claim 21, wherein said oxidizing agent is a peroxo compound.

24. The process as claimed in 23, wherein said peroxo compound is hydrogen peroxide.

* * * * *